United States Patent [19]

Proctor et al.

[11] 4,106,496

[45] Aug. 15, 1978

[54] METHOD AND APPARATUS FOR AIR CALORIC TESTING FOR THE EVALUATION OR AURAL VESTIBULAR DISORDERS

[75] Inventors: Leonard R. Proctor, Baltimore, Md.; Rollin C. Dix, Chicago, Ill.; Werner A. Metz, Atlanta, Ga.

[73] Assignee: The United States of America as represented by the Department of Health, Education and Welfare, Washington, D.C.

[21] Appl. No.: 753,945

[22] Filed: Dec. 23, 1976

[51] Int. Cl.$^2$ ................... A61B 19/00; A61B 10/00
[52] U.S. Cl. .......................... 128/2 R; 128/2 N; 128/2.1 M; 128/401
[58] Field of Search .......... 128/2 R, 2 N, 2 Z, 2.1 M, 128/212, 254–257, 399–402

[56] References Cited

U.S. PATENT DOCUMENTS

| 1,819,941 | 8/1931 | Brown | 128/255 |
|---|---|---|---|
| 3,000,271 | 9/1961 | Harvey et al. | 128/2.1 M |
| 3,563,231 | 2/1971 | Ducote et al. | 128/2.1 M |
| 3,616,796 | 11/1971 | Jackson | 128/212 |
| 3,942,515 | 3/1976 | Servos et al. | 128/2 R |

FOREIGN PATENT DOCUMENTS

| 182,457 | 6/1922 | Guatemala | 128/256 |

OTHER PUBLICATIONS

Proctor et al., "New Approach . . . Receptor", Ann. Otol. 84: 1975, pp. 683–694.
Proctor et al., "Stimulation . . . Aural Inrrigation", Acta Otol. 79: 1975, pp. 425–435.
Capps et al., "Evaluation of the Air Caloric Test . . . , Laryngoscope, vol. 83, Jul. 1973, No. 7, pp. 1013–1021.
Albernaz et al., "The Use of Air . . . Stimulation", Laryngoscope, vol. 82, 1972, pp. 2198–2203.
Aantaa, "Caloric Test with Air", Acto Otol., Supp. 224, vol. 24, 1967, pp 82–85.
Gates et al., "The Thermoelectric Air Stimulator", Acta. Otol., vol. 92, Jul. 1970, pp 80–84.

Primary Examiner—Lee S. Cohen
Attorney, Agent, or Firm—Browdy and Neimark

[57] ABSTRACT

A caloric testing technique and apparatus for evaluating vestibular ear disorders by independently stimulating the left and right lateral canal receptor organs, using heated and cold air, and measuring the responses in order to obtain an indication of disordered vestibular function. Timed irrigation periods are employed, the periods being adjustable so as to control the magnitudes of the caloric stimulations, and the measurements of responses are made by the electrical recording of eye movements for accurate measurement of nystagmic response intensity.

12 Claims, 5 Drawing Figures

METHOD AND APPARATUS FOR AIR CALORIC TESTING FOR THE EVALUATION OR AURAL VESTIBULAR DISORDERS

FIELD OF THE INVENTION

This invention relates to clinical caloric ear testing, and more particularly to a method and apparatus for independent caloric stimulation of either the left or right lateral semi-circular canal receptor organ and for comparing the responses thereto so as to provide an indication of disordered vestibular function.

BACKGROUND OF THE INVENTION

At present the most widely accepted technique for applying aural caloric irrigations for determining disordered vestibular function employs four separate aural irrigations with water at a high flow rate, the water temperature being carefully controlled so as to be at 7° C above and below body temperature. In this technique, all stimulations are of equal strength, in order to detect and measure small differences in excitability between labyrinths, as well as between right-beating versus left-beating nystagmus. This technique has helped to advance the study of vestibular disorders, but further improvements are needed to overcome certain objectionable features of said technique. One problem with said technique is the prolonged duration of each stimulation, which is often stressful to patients and which results in a requirement of long waiting periods between irrigations. Originally it was recommended that a waiting period of at least 9 minutes should separate the onset of successive irrigations, but more recently a 30-minute waiting period has been advised when precise measurements of vestibular responsiveness are desired.

The prolonged duration of the caloric stimulus is caused by a slow exchange of heat between the warmed or cooled labyrinth and surrounding tissues and material, such as blood, temporal bone and skin of the aural canal. With regard to the rate of heat exchange, data obtained from intralabyrinthine temperature measurements made in living human subjects show that temperature disturbances in the labyrinth area caused by conventional caloric irrigations may last for over 10 minutes. According to studies made, it would appear that a weak but persistent caloric stimulus continues to act during the waiting period between conventional irrigations, and may still be present when the next irrigation is commenced. The cessation of nystagmus which occurs in the face of such a persisting caloric stimulus may be the result of an adaptation of the vestibular neural elements. It is possible, therefore, that a residual caloric stimulus may interfere with the results of successive conventional irrigations through a modification of vestibular responsiveness induced by such a prolonged action. Furthermore, most clinicians assess the intensity of the nystagmic response by measuring nystagmus at the peak of the reaction, and therefore a prolonged stimulation would not seem to be required for evaluating vestibular responsiveness.

Another problem with the above-mentioned technique is that there appears to be no convenient means for adjusting the intensity of the stimulus.

SUMMARY OF THE INVENTION

Accordingly, an object of the invention is to overcome deficiencies in the prior art, such as mentioned above.

Another object is to provide for improved testing for vestibular disorders.

Another object of the present invention is to overcome the above-described difficulties by employing a novel and improved irrigation method wherein each stimulation is controlled to be at a previously selected intensity and then promptly to be reduced to zero value; this control of caloric stimulus intensity is accomplished by switching the temperature of a continuous aural irrigation between hot and cold values computed according to a mathematical model of heat conduction in the labyrinth area.

A further object of the invention is to provide an improved aural irrigation method and apparatus wherein the convenience and applicability of the technique is enhanced by using air instead of water as the irrigation fluid, and wherein the temperature of a continuous fluid irrigation is switched by switching two different constant-temperature air supply sources to the aural irrigation nozzle. It has been shown that nystagmic responses of intensity equal to those caused by conventional water irrigation can be produced when using air, provided that greater temperature differences and longer irrigations are employed. For example, air temperatures 13° C above and below body temperature, with a flow rate of 8 liters per minute and irrigation durations of 60 seconds may be employed. Air has been found to be a more convenient irrigation fluid and can be used in the presence of external otitis or tympanic perforation. Similarly, it has been found that air at 51° C and flowing at 8 liters per minute is well tolerated for 60 seconds among normal subjects and that it is therefore feasible to use a 14° C irrigation temperature difference relative to body temperature.

BRIEF DESCRIPTION OF THE DRAWINGS

Further objects and advantages of the invention will become apparent from the following description and claims, and from the accompanying drawings, wherein:

DESCRIPTION OF PREFERRED EMBODIMENTS

Aural irrigation with cold or warm fluid causes a temperature difference ΔT to appear across the lateral semicircular canal. This temperature difference causes a density difference which moves the endolymph-cupula system. The magnitude of endolymph-displacing forces is nearly proportional to the temperature difference across the semicircular canal, so long as the orientation of the canal with respect to gravity is controlled. Therefore, a knowledge of the temperature difference across the lateral semicircular canal permits a direct estimation of the magnitude of the caloric test stimulus.

The temperature difference $\Delta T$ across the lateral semicircular canal may be calculated from a knowledge of irrigation fluid temperature by means of a mathematical model of unidirectional conduction of heat through a homogeneous solid. See G. Schmaltz, "The Physical Phenomena Occurring in the Semicircular Canals During Rotatory and Thermic Stimulation", Proc. R. Soc. Med. 25:359–381, 1932, J. H. Young, "Analysis of Vestibular System Responses to Thermal Gradients Induced in the Temporal Bone", Thesis, Ann Arbor, U. of Michigan, 1972, H. S. Carslaw, J. C. Jaeger, "Conduction of Heat in Solids", Oxford, Oxford University Press, 1959. Furthermore, if the temperature of the irrigating fluid is switched abruptly between hot and cold values, then the timing of this temperature switching can be used to adjust and control the magnitude of the caloric stimulus.

Figure 1:
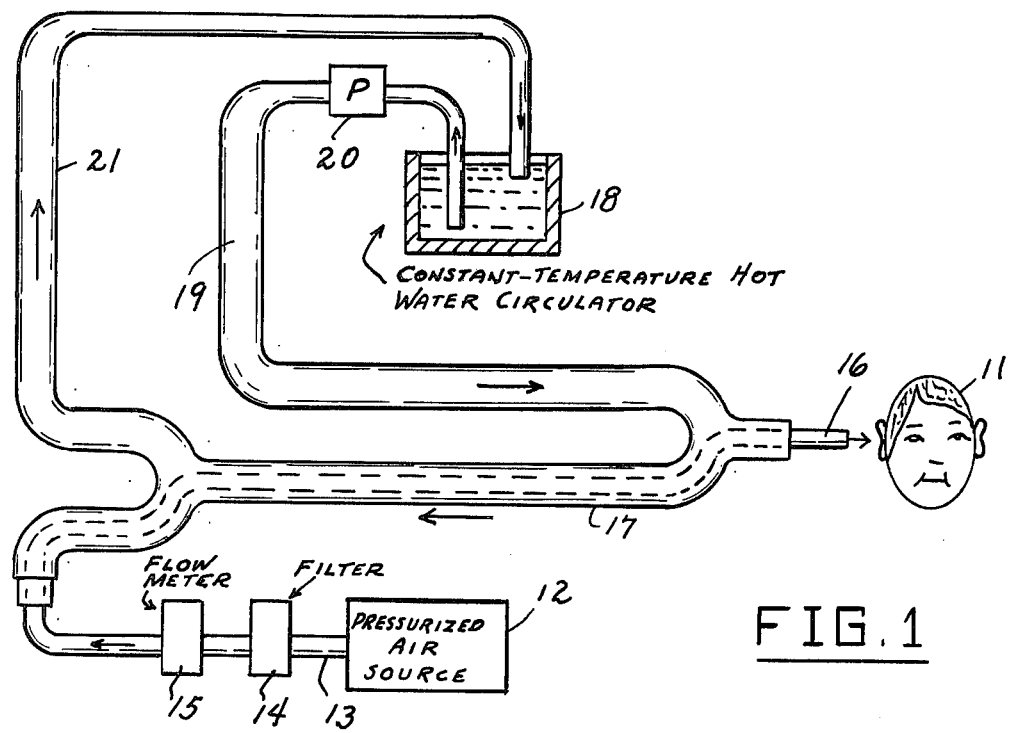
FIG. 1 is a diagrammatic view of a typical air-water heat exchanger with an aural air irrigation nozzle, in accordance with the present invention.

FIG. 1 diagrammatically illustrates a simple caloric air application system including an air-water heat exchanger, according to the present invention, for carrying out a test procedure on a human subject, shown at 11. Air from a pressurized source 12 passes through a conduit 13 including a filter 14 and a flow meter 15 to a discharge nozzle 16 adjacent to and directed toward the subject's ear. The conduit 13 extends through a water jacket 17 which is supplied with water at a constant temperature circulating in a countercurrent direction, relative to air flow, from a constant-temperature bath 18 via a supply conduit 19 including a pump 20, and a return conduit 21.

Figure 2:
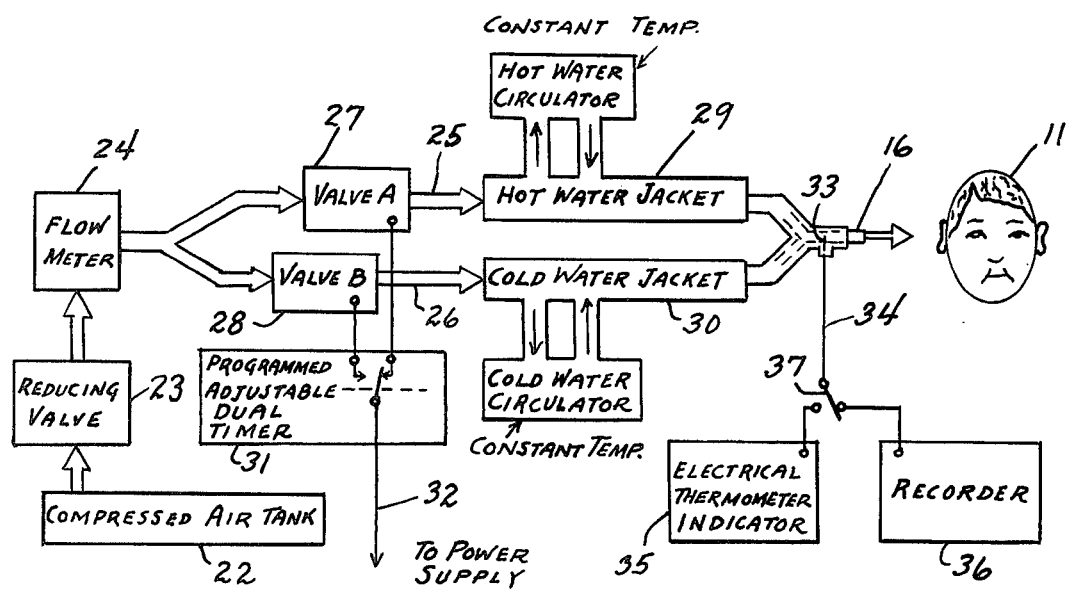
FIG. 2 is a diagrammatic view of an aural air irrigation system according to the present invention, employing hot and cold air, with means for switching air irrigation temperature between hot and cold values at preselected times.

FIG. 2 diagrammatically illustrates a more comprehensive caloric air application system according to the present invention, wherein two heat exchangers are combined with means for rapid switching of the air stream temperature between hot and cold values. Dry air from a compressed air tank 22 is passed through a reducing valve 23 and a flow meter 24, so that it is at controlled pressure, and is supplied thereafter to either a conduit 25 or 26 through an electrically operated control valve 27 or 28. Conduit 25 extends through a hot water jacket 29 to the applicator nozzle 16. Conduit 26 extends through a cold water jacket 30 to said applicator nozzle 16. The electrical valves 27 and 28 are alternately energized (opened) by an electrical timer 31 connected between the valves and a current supply line 32. The timer 31 has conventional adjustable means for setting the respective alternate periods of energization of the control valves 27 and 28. Thus, the valves 27 and 28 are controlled by the adjustable dual timer 31 so that air flow can be started and directed through either the hot or cold water jackets 29 and 30 at appropriate times. A conventional electrical temperature sensor 33 within the nozzle 16 provides constant monitoring of the air stream temperature at a point just before it enters the aural canal. The temperature signal line 34 is selectively connected to either a conventional electrical thermometer indicator 35 or a recorder 36 via a 2-position control switch 37.

Figure 3:
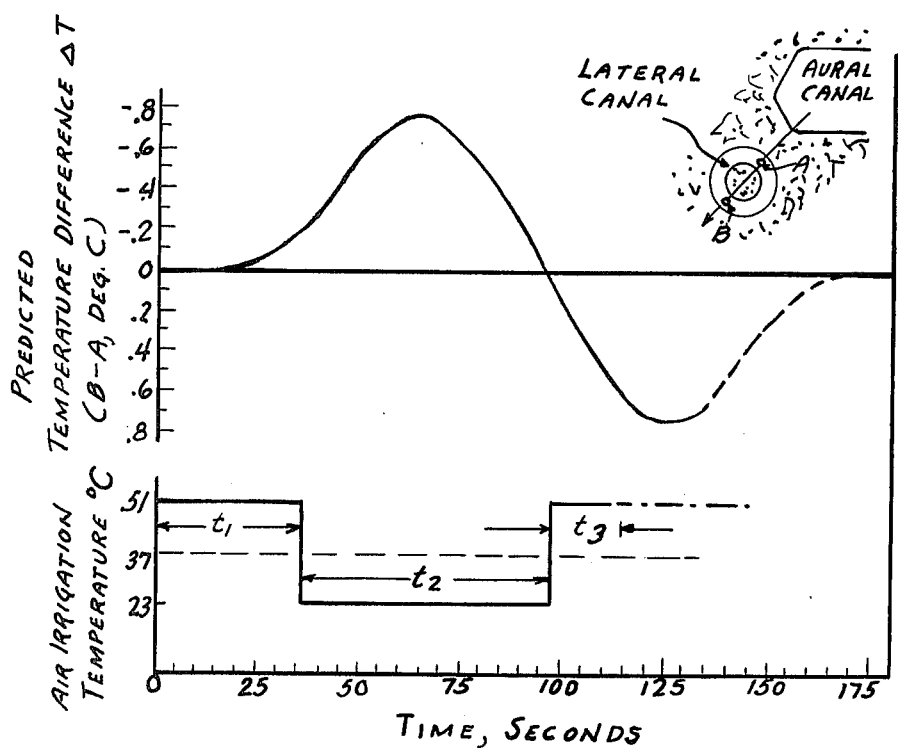
FIG. 3 illustrates typical graphs showing the time course of predicted temperature differences ΔT across a lateral semi-circular canal produced by step temperature changes during continuous aural irrigation with air, employing the system of FIG. 2, with the time course of air irrigation temperature shown in the lower graph and the predicted temperature difference ΔT shown in the upper graph.

In a typical application of the method of the present invention, using the system shown in FIG. 2, aural irrigation was begun with air at 51° C, switched to 23° C, and then switched back to 51° C (see FIG. 3). Under these conditions, the duration of the initial 51° C irrigation ($t_1$) determined the magnitude of the caloric stimulus produced during the initial hot phase of the stimulation. In a similar way, the duration of the second irrigation ($t_2$) determined the magnitude of the resulting caloric stimulus during the cold phase of the reaction. The durations of the irrigations ($t_1$ and $t_2$) were carefully calculated by means of a computerized search procedure (see B. Carnahan, H. A. Lather, J. P. Wilkes, "Applied Numerical Methods", New York, John Wiley, 1969), using the mathematical model mentioned above. Values for physical parameters used were determined from the publication of J. H. Young, mentioned above, except for a 30% reduction in the heat transfer coefficient, a modification based on preliminary trials among normal subjects.

The calculations from the search procedure indicated that irrigation with 51° C air for 36 seconds ($t_1$), switching to 23° C air for 61 seconds ($t_2$), and then switching back to hot air ($t_3$) would produce the changes in the value of $\Delta T$ shown in FIG. 3. The time course of the temperature difference across the lateral semicircular canal is seen to describe a roughly sinusoidal pattern, reaching equal peak values in the hot and cold phases of the reaction. The aural irrigation sequence required to produce such a $\Delta T$ curve is shown in the lower part of the figure. As can be seen in FIG. 3, calculations based upon the mathematical model predict a time lag between changes in the irrigation temperature and the effects of such changes upon the value of $\Delta T$ across the semicircular canal. This is in agreement with actual temporal bone temperature recordings. Thus, a significant temperature difference does not appear until 20 seconds after starting the irrigation. Also, the effect of the hot irrigation continues to predominate for over 20 seconds after switching to a cold irrigation.

The computerized search procedure can be used to determine sets of values for irrigation durations $t_1$ and $t_2$ required to produce a desired graded series of stimulus magnitudes. Thus, the caloric stimulus can be controlled and adjusted in a consistent manner by employing the appropriate set of irrigation durations.

In using the apparatus of FIG. 2 to carry out the technique of the present invention, a selected set of irrigation durations $t_1$ and $t_2$ is employed with a patient 11, and a biphasic nystagmus pattern is recorded, using conventional eye movement sensing and recording apparatus providing an electronystagmographic curve or trace. In actual tests, the mean slow phase eye speed calculated for each 5 seconds of the nystagmus pattern of response, plotted as a function of time conformed generally with the $\Delta T$ curve of FIG. 3.

One way to gain information about the vestibular responses of a subject is to compare his responses to weak stimulations with those produced by stronger stimulations. In order to perform this type of test, it is convenient to change the biphasic stimulus pattern to a monophasic one. Thus, the aural irrigation sequence is arranged so that only the first (hot) phase of the stimulus appears. For monophasic testing, the irrigation temperature is switched only once, thereby simply terminating the initial (hot) irrigation with a brief cold irrigation. The duration of the hot irrigation ($t_1$) is the determinant of the peak $\Delta T$ value. The duration of the cold irrigation ($t_2$) is estimated with the intention of reducing $\Delta T$ to zero value as quickly as possible. Obviously, in this procedure the values of $t_1$ for various monophasic stimulus strengths are the same as the biphasic $t_1$ values, and monophasic $t_2$ values correspond to biphasic $t_3$ values (see FIG. 3).

Figure 4:
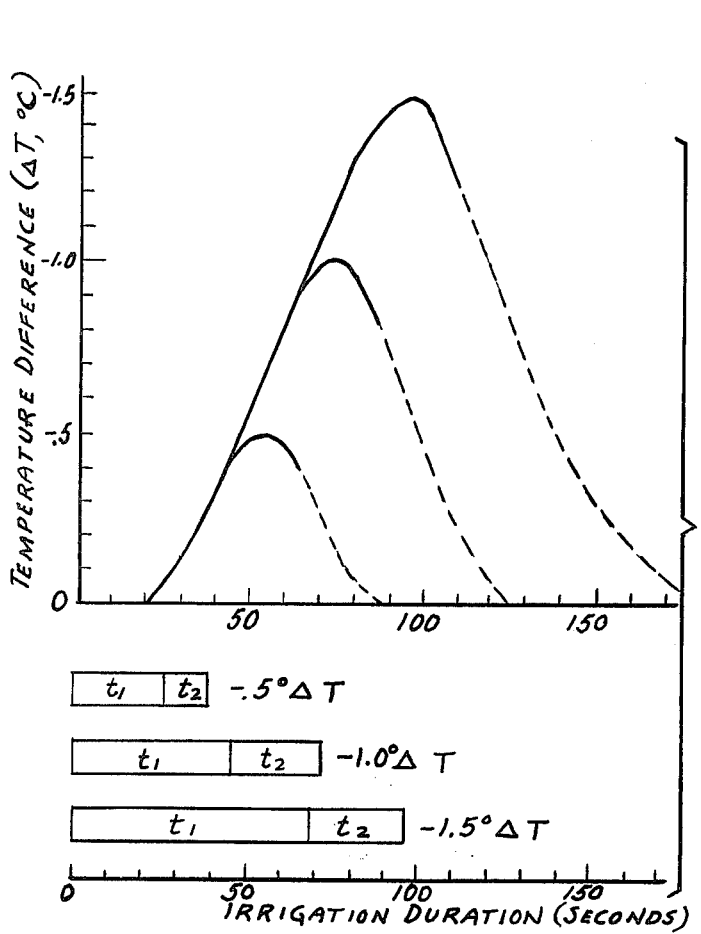
FIG. 4 illustrates graphs showing monophasic temperature differences across a lateral semicircular canal predicted to result from application of various irrigation durations.

FIG. 4 illustrates the time courses of monophasic stimulations, with corresponding irrigation sequences. An irrigation duration of $t_1 = 69$ seconds is predicted to induce a peak $\Delta T$ value of 1.5° C. Similarly, $t_1$ values of 46 and 27 seconds respectively produce peak $\Delta T$ values of 1.0° C and 0.5° C, as shown in FIG. 4.

Figure 5:
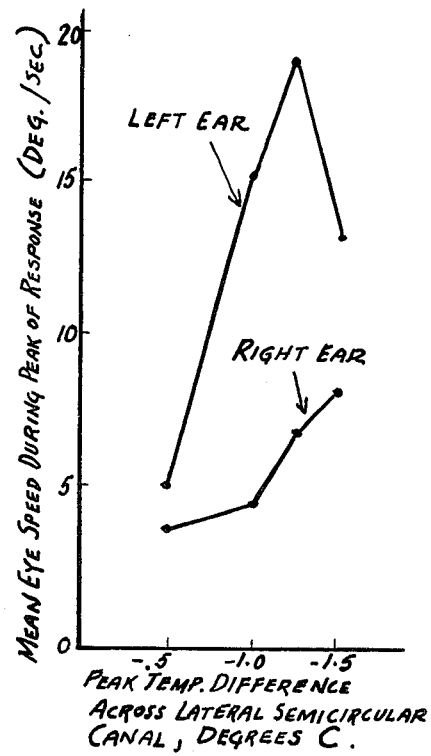
FIG. 5 shows nystagmus response curves for the right and left ear of a patient, wherein the right ear exhibits vestibular abnormality.

Using a series of independent monophasic stimulations of increasing magnitudes provides a way of measuring nystagmus response intensity as a function of stimulus intensity, and can be employed to compare responses of the right ear with those of the left ear, to thereby detect and diagnose abnormalities causing reduced response, such as vestibular neuronitis. For example, biphasic air tests may first be conducted, and then monophasic air tests may be applied alternately to both ears, in strengths of 0.5° C, 1.0° C, 1.25° C and 1.5° C, and nystagmus response curves may be recorded therefrom. The average slow phase eye speed during a 20 seconds period at the peak of each monophasic response and during the peak of the hot phase of the biphasic response may be calculated. FIG. 5 typically shows the result of such tests and calculations, wherein stimulations of increasing magnitude in the right ear produce a set of responses substantially less than those from the left ear, indicating a vestibular abnormality in the right ear.

From the above description it will be seen that the principal advantages of the caloric irrigation technique of the present invention are the reduced duration of action of the caloric stimulus and the practical and convenient means employed for adjusting the intensities of the individual stimulations. Prompt removal of the caloric stimulus permits a reduction in the waiting time between irrigations, as well as reduces interaction among successive stimulations. The provision of means to adjust the stimulus intensity conveniently is an important feature of the improved system employed in the present invention. Stimulus intensity can be easily reduced for those subjects who are unusually sensitive, or increased when responses are feeble. In addition, a series of stimulations of various intensities may be applied to explore other aspects of vestibular responsiveness. The $T_3$ irrigation may be of a duration to produce a third temperature difference across the canal passage; this duration being differenet than the $t_1$ duration. After the $T_3$ irrigation the canal may again be flushed with cold air to reduce $\Delta T$ to zero.

While certain specific embodiments of an improved aural caloric irrigation technique and apparatus for performing same have been disclosed in the foregoing description, it will be understood that various modifications within the spirit of the invention may occur to those skilled in the art. Therefore it is intended that the invention is not limited to the embodiments disclosed, and that modifications may be made without departing from the scope of the invention.

What is claimed is:

1. A method of stimulating an aural lateral canal passage for evaluating vestibular responsiveness comprising the steps of irrigating the canal with air heated to a precise and controlled temperature above the body temperature for a brief period of time sufficient to develop a predetermined temperature difference across the canal passage, then promptly removing said heated air at the end of said brief period and irrigating the canal for a brief period unequal to the first brief period with relatively cold air precisely controlled at a temperature below body temperature, to first reduce said temperature difference to zero and then produce a second temperature difference across the canal passage, and then again irrigating the canal with said precisely heated hot air for a brief but different period of time than said initial period of time, to first reduce said second temperature difference to zero and then produce a third temperature difference across the canal passage.

2. The aural stimulation method of claim 1, and wherein said heated and cold air differ from body temperature by approximately the same amount.

3. The aural stimulation method of claim 1, and wherein the irrigation of the canal is at a substantially constant flow rate.

4. The aural stimulation method of claim 1, and wherein said heated and cold air each differ from body temperature by approximately 14° C.

5. The aural stimulation method of claim 1, and adjusting the temperature differences derived across the canal passage by varying the durations of irrigation with heated air.

6. The aural stimulation method of claim 1, and then again irrigating the canal with said relatively cold air sufficiently to reduce said last-named temperature difference to zero.

7. A method in accordance with claim 1, wherein said brief periods are no greater than about 1 minute, using an air flow rate of about 8 liters per minute.

8. An apparatus for stimulating an aural lateral canal passage comprising a source of pressurized air, means for directing air to the ear including a nozzle member, a first conduit connecting said nozzle member to said source, first heat exchange jacket means surrounding said conduit, a precisely controlled constant temperature heated liquid container, means to circulate heated liquid from said heated liquid container through said jacket means for heating the air in the first conduit; a second conduit connecting said source to said nozzle member, second heat exchange jacket means surrounding said second conduit, a precisely controlled constant temperature cold liquid container, means to circulate cold liquid from said cold liquid container through said second jacket means to cool the air in the second conduit, means to selectively control flow of air from said source through said first and second conduits; and temperature sensing and indicating means including a temperature sensor in said nozzle member.

9. The stimulation apparatus of claim 8, and wherein said selective control means comprises respective valves in said first and second conduits.

10. The stimulation apparatus of claim 9, and wherein said valves are of the electrical type and are provided with energizing means, and circuit means including selector switch means connecting said energizing means to said valves.

11. The stimulation apparatus of claim 10, and wherein said selector switch means comprises a timer switch which is adjustable to set the durations of energization of the valves to variable periods of time.

12. Apparatus in accordance with claim 8 comprising a Y-shaped fitting connecting said nozzle member with each of said first and second conduits.

* * * * *